United States Patent
Sommermeyer

(10) Patent No.: US 7,115,576 B2
(45) Date of Patent: Oct. 3, 2006

(54) WATER-SOLUBLE ANTIBIOTIC COMPRISING AN AMINO SUGAR, IN THE FORM OF A POLYSACCHARIDE CONJUGATE

(75) Inventor: Klaus Sommermeyer, Rosbach (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 15 days.

(21) Appl. No.: 10/481,597

(22) PCT Filed: Jun. 19, 2002

(86) PCT No.: PCT/EP02/06764

§ 371 (c)(1),
(2), (4) Date: Dec. 19, 2003

(87) PCT Pub. No.: WO03/000738

PCT Pub. Date: Jan. 3, 2003

(65) Prior Publication Data

US 2004/0180858 A1    Sep. 16, 2004

(30) Foreign Application Priority Data

Jun. 21, 2001 (DE) ................. 101 29 369

(51) Int. Cl.
*A61K 31/70* (2006.01)
*C07H 15/24* (2006.01)
*C07H 17/08* (2006.01)

(52) U.S. Cl. ............... 514/31; 514/34; 536/6.4; 536/6.5

(58) Field of Classification Search ........... 536/6.4, 536/6.5; 514/31, 34
See application file for complete search history.

(56) References Cited

U.S. PATENT DOCUMENTS 6,011,008 A    1/2000    Domb et al.

FOREIGN PATENT DOCUMENTS

| EP | 0 428 486 A1 | 11/1990 |
|---|---|---|
| WO | WO 98/07536 | 4/1994 |
| WO | WO 98/01158 | 1/1998 |
| WO | WO 98/56424 | 12/1998 |
| WO | WO 00/78355 A2 | 12/2000 |
| WO | WO 02/02146 A2 | 1/2002 |
| WO | WO 02/080979 A2 | 10/2002 |
| WO | WO 02/090390 A1 | 11/2002 |

OTHER PUBLICATIONS

Cera, C., et al., "Water-soluble polysaccharide-anthracycline conjugates: biological activity," *Anti-Cancer Drug Design*, 7:143-151 (1992).
Ehrenfreund-Kleinman, T., et al., "Synthesis and characterization of novel water soluble amphotericin B-arabinogalactan conjugates," *Biomaterials*, 23:1327-1335 (2002).
Falk, Rama, et al., "A Novel Injectable Water-Soluble Amphotericin B-Arabinogalactan Conjugate," *Antimicrobial Agents and Chemotherapy*, 42(8):1975-1981 (1999).
Abstract No. XP-002238925, "Antitumor Composition Retain Body Long Period Antitumor Agent Amino Group Fix Insoluble Polysaccharide".

*Primary Examiner*—Elli Peselev
(74) *Attorney, Agent, or Firm*—Hamilton, Brook, Smith & Reynolds, P.C.

(57) ABSTRACT

The invention relates to novel pharmaceutical forms for antibiotics containing amino sugar, amphotericin B, daunorubicin and doxorubicin, in which the known side effects are reduced and which can be used in a simple manner. The antimycotic agent B is nephrotoxic. The cytostatic agents daunorubicin and doxorubicin are highly cardiotoxic. The novel pharmaceutical forms are antibiotic-starch conjugates, wherein the antibiotic is combined with the polysaccharide at the reducing end thereof by means of a peptide bond. According to the invention, said bond is carried out by means of $J_2$ oxidation of the starch derivative at the reducing end thereof in an aqueous alkaline solution, and by coupling the starch derivative oxidised thereby to the antibiotic in an organic solution. The conjugates obtained are less toxic. The polysaccharide part can be decomposed by serum-α-amylase and the peptide bond can be accessed by an enzymatic attack.

42 Claims, No Drawings

WATER-SOLUBLE ANTIBIOTIC COMPRISING AN AMINO SUGAR, IN THE FORM OF A POLYSACCHARIDE CONJUGATE

RELATED APPLICATIONS

This application is the U.S. National Phase of International Application No. PCT/EP02/06764, filed 19 Jun. 2002, published in German, which application claims priority under 35 U.S.C. § 119 or 365 to German Application No. 101 29 369.0, filed 21 Jun. 2001. The entire teachings of the above application are incorporated herein by reference.

The present invention relates to water-soluble, orally or parenterally administrable preparations of antibiotics comprising an amino sugar, in the form of a conjugate with a polysaccharide based on starch or starch derivatives, in particular hydroxyethyl starch and hydroxypropyl starch, and a method for their cost-effective preparation in high yield. Particularly preferred as polysaccharide is hydroxyethyl starch. Amphotericin B, daunorubicin and doxorubicin, which all comprise an amino group in the $C_3$ position of the amino acid part, are particularly considered as antibiotics with an amino sugar.

The antibiotics containing amino sugar, amphotericin B, daunorubicin and doxorubicin, are widely used in therapy and often represent the agent of choice, although they display serious side effects in some cases. Amphotericin B is administered primarily parenterally, daunorubicin and doxorubicin must necessarily be administered intravenously.

Amphotericin B is a polyene antibiotic isolated from *Streptomyces nodosus*. Chemically, it is a macrocyclic lactone (macrolide) with 7 conjugated double bonds in all-trans configuration within a 38-member lactone ring to which the amino sugar D-mycosamine is bound via an O-glycosidic bond. Amphotericin B is amphoteric and has lipophilic and hydrophilic regions in the molecule which enable it to form complexes with the sterols present in the cytoplasma membrane of fungi, which leads to impairment of cell permeability. As bacterial membranes do not contain sterols, the antibiotic action of amphotericin B is selectively directed at fungi.

On the other hand, the use of amphotericin B is associated with side effects that are sometimes relatively massive. In generalised mycoses and organ mycoses, amphotericin B is administered intravenously, usually with a daily dose of 0.5 to 0.7 mg/kg body weight. Since, however, the tolerability of amphotericin B varies from patient to patient, the dosage must be individually adjusted or adapted. In addition, patients with an impaired immune system require generally higher doses than usual, for example 1 mg/kg body weight daily, which in severe forms—where well tolerated—can be increased to up to 1.5 mg/kg. The duration of parenteral administration may in this connection extend from several weeks to several months.

In the course of a parenteral treatment, reactions typical of infusion usually occur, such as for example fever, vomiting and shivering attacks, which are usually treated symptomatically so that interruption of the infusion treatment is unnecessary. More serious are, however, the frequently occurring hepatic and in particular renal dysfunctions. Thus, for example, at the beginning of therapy, the glomerular filtration rate always falls by around 40%. In the majority of those treated, it remains lowered throughout the therapeutic period. Accordingly, creatinine in the serum and urea in the blood rise. Occasionally, irreversible damage is even observable beyond the therapeutic period. After two to three weeks of treatment, anaemia also occurs frequently, which can lead to haematocrit levels of 25 to 30%. The blood count changes are, however, generally fully reversible again after the end of the therapy.

Owing to its toxicity and side effects, amphotericin B should therefore be administered only in life-threatening circumstances. On the other hand, it often represents the only effective agent in mycoses arising from disturbances of the immune system—for example, in AIDS or after organ transplants.

Despite hydrophilic domains within the molecule, amphotericin as a whole displays marked hydrophobic properties, so that it is virtually insoluble in the physiological pH range in water. Even in organic solvents, it is only sparingly soluble. As a result, current commercially available preparations represent pharmaceutical forms of relatively complex structure that are encumbered by additional disadvan- Amphotericin B

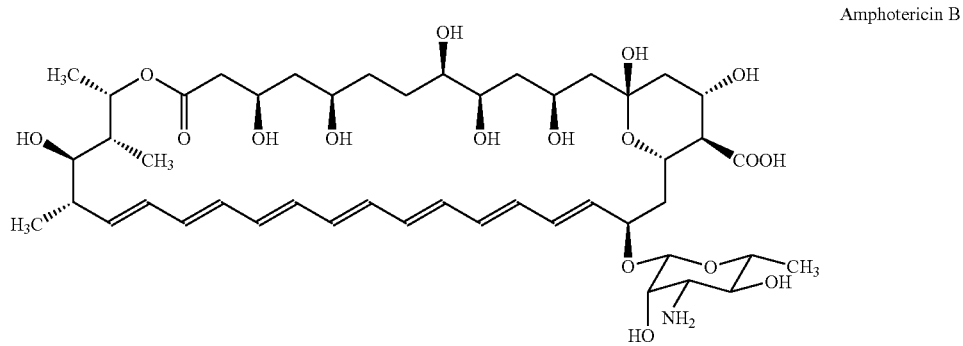

Owing to the broad spectrum of action of amphotericin B, which encompasses virtually all fungi that are pathogenic to humans, it is the agent of choice for the systemic treatment of mycotic infections in humans. Particularly in patients whose immune system is impaired, such as HIV or cancer patients, treatment of the associated invasive fungal infections has increased sharply in recent years.

tages. With a suitable solubiliser, such as Na-deoxycholate, solubility in water can be increased. Thus, for example, the originator preparation produced by BRISTOL-MYERS SQUIBB intended for infusion (available in Germany with the commercial name "Amphotericin B") exists as dry substance, which must be reconstituted in water and then takes the form of a micellar dispersion of amphotericin B and Na-deoxycholate in water. To obtain an infusion solution ready for administration, the stock solution thus obtained can be diluted only with electrolyte-free carrier solutions, such as for example a 5% glucose solution, to the desired final concentration.

This preparation also exhibits only a very limited therapeutic index, i.e. the window between effective and toxic doses is very narrow. In addition, despite the relatively broad spectrum of action of amphotericin B, this preparation is less effective in certain clinical pictures because the active substance does not reach the site of the mycotic infection or does so only in insufficient concentrations, so that amphotericin B cannot display its characteristic antifungal action there, or can only do so insufficiently.

To overcome these disadvantages of the originator preparation, a series of amphotericin B preparations have been developed that represent lipid formulations, for example lipid complexes with amphotericin B, colloidal dispersions of cholesteryl sulphate with amphotericin B and liposomally packed amphotericin B. Although all these pharmaceutical forms display a greater therapeutic index and higher tolerance, in particular lower nephrotoxicity compared with a conventional amphotericin B deoxycholate formulation, which is why they can also be administered in higher doses, the side effects described above cannot be entirely avoided in high doses.

A serious disadvantage of such lipid formulations of amphotericin B lies, however, in the very high production costs and the associated commercial prices. In addition, these complex pharmaceutical forms must continue to be reconstituted in an elaborate way to provide their form ready for administration. Not least of all owing to these disadvantages, broad acceptance on the market has failed to materialise despite the improved therapeutic range in lipid formulations of amphotericin B.

As a further method for transforming amphotericin B into a water-soluble form for injection purposes, the formation of an amphotericin B-arabinogalactan conjugate is described in the literature (Antimicrobial Agents and Chemotherapy, Vol. 43 No. 8, 1999, 1975–1981). Arabinogalactan is a water-soluble polysaccharide obtained from larches and comprised of arabinose and galactose units in a ration of 1:6. The bonding of amphotericin B to arabinogalactan takes place in 4 steps. First of all, arabinogalactan is subjected to periodate oxidation, with vicinal hydroxyl groups of the sugar units being transformed with ring cleavage into dialdehydes. Following purification of the reaction products via an anion exchanger column, the amino group of the mycos amine of amphotericin B is, with the formation of an imine (Schiff base), coupled to an aldehyde group and lastly, via reduction with the aid of Na boron hydride, the imine group is transformed into an amine group and unreacted aldehyde groups into hydroxyl groups.

The coupling reaction is performed at pH 11. This pH value represents a compromise between the yield of the conjugate formed on the one hand and the toxicity of the conjugate on the other. Below pH 10, amphotericin B is insoluble in water and yields are low. Upwards of a pH of 12, amphotericin B is relatively water-soluble, which permits higher yields, but the product obtained is toxic. Toxicity was also observable if the last stage of the Na boron hydride reduction was omitted.

The antibiotics daunorubicin and doxyrubicin belong to the group of anthiacyclines and differ only in terms of a hydroxyl group. They are soluble in water. Doxorubicin is obtained from cultures of the fungus *Streptoniyces peuceticus* var. *caesius*, daunomycin from *Streptomycin peuceticus* or *coeruleorubidus*.

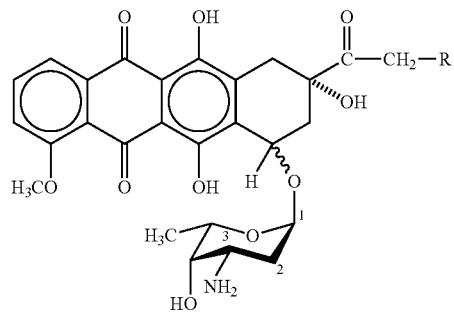

Daunorubicin: R=H
Doxorubicin: R=OH

By virtue of their tetracycline radical, daunorubicin and doxorubicin are capable of inhibiting DNA and RNA synthesis, with the formation of highly stable DNA intercalation complexes that are resistant for a relatively long while. In addition, they form, in connection with their intracellular metabolisation with the aid of cytochrome P-450 reductase and NADPH, semiquinone radicals, which for their part trigger further radical reactions (superoxide anion and hadroxyl radicals). These antibiotics thereby acquire a marked cytostatic action, as a result of which they are used as cytostatics in cancer therapy.

As these antibiotics are only inadequately absorbed after oral administration, they must be administered (strictly) intravenously in short infusions for 10 to 15 minutes. Their distribution in the body proceeds rapidly, with the highest concentrations having been found in the heart, lungs, spleen and kidneys.

Their rapid distribution in the body in connection with the formation of reactive radicals by metabolisation seems to be one of the causes of the marked toxic side effects, as a result of which in particular the heart is affected detrimentally.

Both doxorubicin and daunorubicin are markedly cardiotoxic. Particularly the cardiotoxicity of the late type, which represents dose-dependent cumulative organ toxicity, is as a rule irreversible and often life-threatening. If a maximum cumulative total dose, which in adults is 550 mg/m$^3$ body surface area, is exceeded, the incidence of the anthracycline-induced cardiomyopathy increases rapidly. Upwards of a total dose of 550 mg/m$^3$ body surface area, an approximately 5% risk therefore exists for the occurrence of severe cardiac insufficiency. If this cumulative total dose is achieved, the therapy must be discontinued.

The aim of the present invention is therefore to make available for such amino sugar-containing antibiotics pharmaceutical forms in which the specific toxic side effects are reduced, which guarantee more uniform, controlled distribution in the body and thus allow a higher dosage and which are nevertheless easy to use. A further aim of the invention consists in making available a cost-effective method for the production of this pharmaceutical form with a high yield.

Surprisingly, it was found that these aims can be achieved with a conjugate of starch or starch derivatives with such antibiotics. The pharmaceutical form according to the invention is a water-soluble antibiotic derivative comprising an amino sugar, in the form of a polysaccharide conjugate of the general form (I)

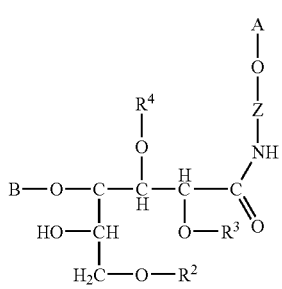 (I)

where:
B=a polymer combined in a 1,4 linkage, selected from the group hydroxyethyl starch, hydroxypropyl starch, soluble amylose, soluble amylose in hydroxyethylated and/or hydroxypropylated form, soluble amylopectin, and soluble amylopectin in hydroxyethylated and/or hydroxypropylated form, $R^2 =$ $H_1(CH_2)_2-OH$, $CH_2-\underset{OH}{\overset{CH_3}{\underset{|}{CH}}}$ or B, $R^3$, $R^4$ independently of one another $H_1(CH_2)_2-OH$ or $CH_2-\underset{OH}{\overset{CH_3}{\underset{|}{CH}}}$ with the conditions that
B=amylose or amylopectin, if $R^2=R^3=R^4=H$
B=hydroxyethyl starch, hydroxyethylated amylopectin or hydroxyethylated amylose, if $R^2$, $R^3$, $R^4=(CH_2)_2-$OH,
B=hydroxypropyl starch, hydroxypropylated amylopectin or hydroxypropylated amylose, if $R^2$, $R^3$,

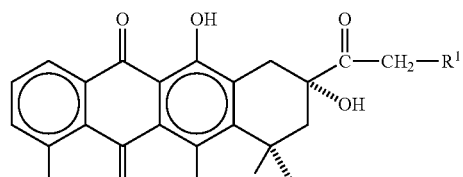

A is

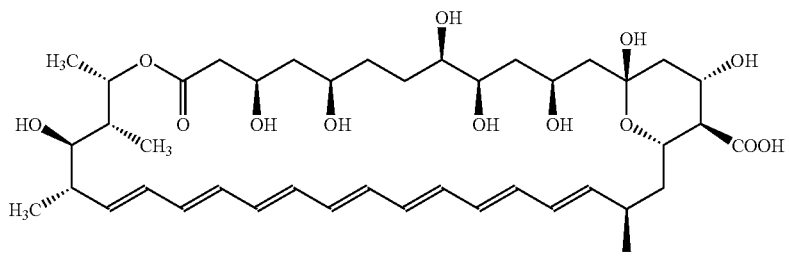

with $R^1=$H or OH or and

Z is 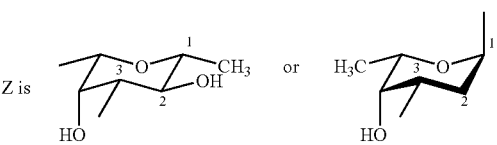

Z is
with the condition that if $Z =$ 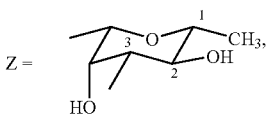

then

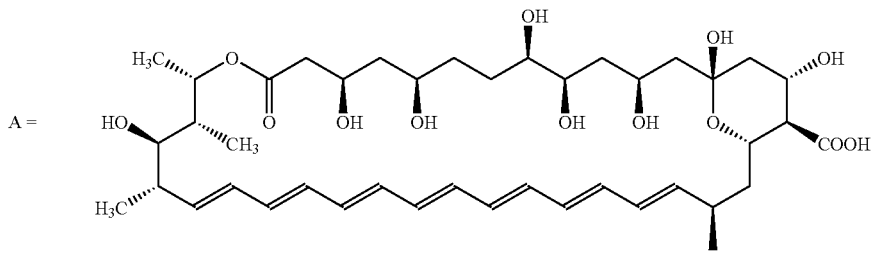

and if

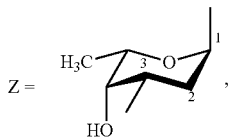

then

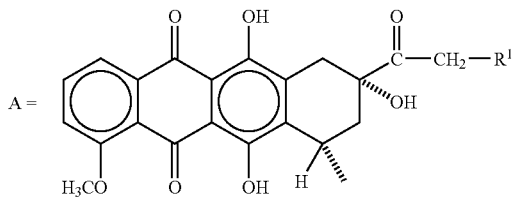

with R¹=H or OH, with the polysaccharide part of the conjugate being combined with the amino group at $C_3$ of the amino sugar of the antibiotic with formation of a peptide bond.

Amylose (unbranched only with α-1,4-glycosidic linkage) and/or amylopectin (branched, additionally with α-1,4-glycosidic linkage) and in particular hydroxyalkylated starch are considered as starch or starch derivatives. If amylose or amylopectin is used, commercially available "soluble" starch is used. The latter may also exist in hydroxyethylated and hydroxypropylated form.

In connection with the preferred use according to the invention of the hydroxyalkylated starches hydroxyethyl starch and hydroxypropyl starch, the mean molecular weight (weight—mean $M_w$) may be in the range between 2000 and $2 \cdot 10^5$ Daltons. The mean degree of polymerisation is, however, to be at least 15 and in a preferred embodiment extend to around 3000 (corresponding to a mean molecular weight of around $5 \cdot 10^5$). Particularly preferred is the use of hydroxyethyl starch.

The statements made below in relation to hydroxyethyl starch as a particularly preferred embodiment apply analogously to hydroxypropyl starch as well.

In an antibiotic-HES conjugate according to the invention, the molecular weight of the HES should preferably be above the renal threshold for HES, i.e. above 70000 Daltons. Particularly preferred is an HES with the specification 130/with a mean molecular weight of 130000 Daltons. The degree of substitution MS is preferably in the range 0.1 to 0.8. In a preferred embodiment, the degree of substitution is in the range 0.3 to 0.5. The preferred $C_2/C_6$ ratio is in the range from 2 to 12, in a particularly preferred embodiment in the range from 5 to 11. In this connection, HES may be present both in unbranched form only with predominantly α-1,4-glycosidic linkages and in branched form with both α-1,4-glycosidic linkages and α-1,6-glycosidic linkages.

In a conjugate according to the invention, bonding of the polysaccharide is according to the method effected to the amino group of the amino sugar of the antibiotic by the free, reducing aldehyde group of the terminal polysaccharide molecule, preferably with $J_2$, being oxidised to an aldonic acid group, which for its part forms with a free hydroxyl group of the terminal sugar unit, preferably at the $C_4$ atom of the terminal sugar unit, a lactone ring which can then form a peptide bond with the amino group of the amino sugar of the antibiotic. Unlike the formation of a Schiff base from the aldehyde radicals of the arabinogalactan that originate from periodate oxidation with the amino group of the amino sugar, the coupling reaction according to the invention of the oxidation product at the reducing end of HES can be performed with the amino group of the amino sugar (e.g. mycosamine in the case of amphotericin B) with a high yield in an organic solvent, e.g. DMSO, in which for example the antibiotic amphotericin B is soluble.

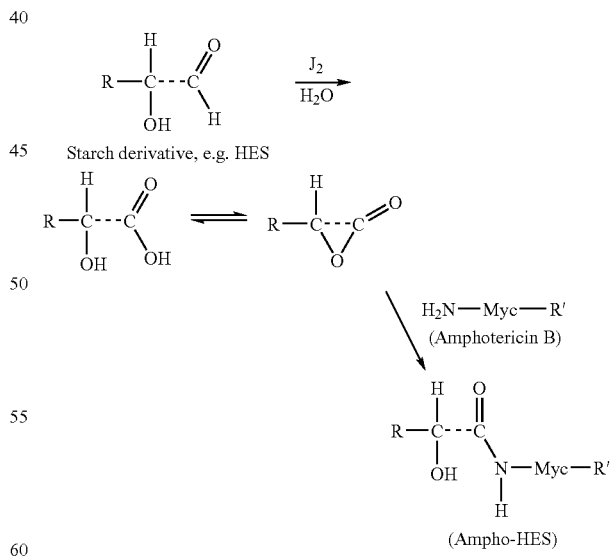

Starch derivative, e.g. HES

This coupling reaction proved to be extraordinarily selective and led with a high yield to an antibiotic-starch conjugate which, unlike in periodate oxidation, results in a molar ratio between antibiotic and polysaccharide of 1:1.

The conjugate obtained surprisingly proved also to be non-toxic, so that it can also be administered orally. The coupling of the polysaccharide carrier, particularly of HES, to the antibiotic resulted, even in the case of inherently water-insoluble amphotericin B, in the conjugate as a whole having adequate water solubility. This means that the dissolution of the conjugate or the dilution to the desired administrable final concentration can be performed also with electrolyte-containing solvents or mixtures (e.g. a mixture of isotonic saline solution and glucose solution). Since, in addition, the conjugate obtained is no longer toxic, higher doses, e.g. for the amphotericin B conjugate daily doses of up to 15 mg amphotericin B fraction, can thus be administered.

Since hydroxyethyl starch can anyway be administered intravenously in high doses as plasma expander, unreacted fractions of HES are physiologically safe in connection with the coupling of HES and amphotericin B and therefore do not need to be specifically separated from the reaction product, which is of considerable economic benefit in synthesis. In the case of amphotericin B, no concluding hydration is required either to render the conjugate formed less toxic. In addition, it was surprisingly found that unbound hydroxyethyl starch inherently even exerts a solubilising effect on amphotericin B, as a result of which additional stabilisation of the antimycotic active substance can be achieved with excess HES.

A further advantage of an antibiotic-HES conjugate according to the invention consists in the fact that the polysaccharide fraction can be broken down by serum α-amylase. This breakdown is described in detail in the relevant literature on the pharmacokinetics of the HES used as plasma expander. In addition, the peptide bond between the polysaccharide fraction and the antibiotic in vivo is in principle accessible to enzymatic attack.

As shown by investigations on *Candida albicans*, known as the indicator micro-organism from the spectrum of possible fungal infection pathogens, the conjugates of amphotericin B according to the invention displayed the activities comparable to the lipid formulations. In the haemolysis test on sheep erythrocytes, it was able to be demonstrated that the in vitro toxicity of an amphotericin B-HES conjugate is considerably less than in commercially available amphotericin B deoxycholate formulations.

A decisive advantage of an antibiotic-HES conjugate according to the invention can be seen in the fact that by the appropriate choice of molecular weight, degree of substitution, substitution pattern and degree of branching of the HES used, the pharmacokinetic properties of the conjugate obtained can be virtually tailored to the needs of a particular patient.

In the following examples, the production method and the haemolytic action of the preferred antibiotic-HES conjugates are elucidated in greater detail.

EXAMPLE 1

Oxidation of HES 130 kD:

10 g HES (130 kD) are placed in a reaction vessel and rendered soluble in the smallest possible volume of water. 2 ml of a 0.1 N iodine solution [and] approx. 3 ml of a 0.1 N NaOH solution are added to this solution while stirring (magnetic stirrer). The mixture is stirred until the colour indicating $I_2$ has disappeared. The addition of iodine solution and/or NaOH solution is repeated several times until a total of 10 ml 0.1 N iodine solution and 20 ml 0.1 N NaOH solution have been added. The solution obtained is then added via an H+ ion exchanger column (Amberlite IR 120) and subsequently dialysed against distilled water in a dialysis tube with an exclusion limit of 4–6 kD for a period of 20 hours. The dialysed product is lyophilised and the degree of oxidation is determined by SOMOGYI's method.

Determination of the degree of oxidation:

To determine the oxidised HES (ox-HES) formed, SOMOGYI's method was adopted (Meth. Carbohydrate Chem., I, 384–386, 1962). The method is based on determination of the free aldehyde groups via the reduction of $Cu^{2+}$ to $Cu^+$. $Cu^+$ is oxidised to $Cu^{2+}$ again with the aid of iodine formed from iodide and iodate. Excess iodine is then titrated by means of thiosulphate.

EXAMPLE 2

Synthesis of an Amphotericin B-HES Conjugate:

In a reaction vessel, 650 mg ($1.5 \cdot 10^{-5}$ mol) dried ox-HES (130 kD, degree of oxidation approx. 100%) and 2.8 mg ($3.0 \cdot 10^{-6}$ mol) amphotericin B are dissolved in approx. 4 ml anhydrous DMSO at room temperature in an $N_2$ atmosphere while stirring at the same time. With light exclusion, the mixture is allowed to react at 70° C. for 24 hours. Processing of the reaction product is performed with light exclusion after the addition of 10 volumes of $H_2O$ by means of dialysis against $H_2O$ at 4° C. for a period of 48 hours, with the water being changed four times. The subsequently lyophilised product yielded a weakly yellowish powder.

The coupling method was repeated with 3 further batches, with a reproducible yield of >90% being obtained for the coupling reaction. The results are set out in Table 1. (The yield quantities indicated in the last column of this table are based on the coupling product plus unreacted HES).

TABLE 1

|  | oxHES | Ampho B | anhydrous DMSO | Reaction time and temperature | Reaction conditions | Yield of ampho-HES after dialysis |
|---|---|---|---|---|---|---|
| Batch 1 | 650 mg ($1.5 \cdot 10^{-5}$ mol) | 2.8 mg ($3.0 \cdot 10^{-6}$ mol) | ≈4 ml | 24 h 70° C. | in the dark under $N_2$ | 460 mg |
| Batch 2 | 10.0 g ($2.4 \cdot 10^{-4}$ mol) | 44.0 mg ($4.7 \cdot 10^{-5}$ mol) | ≈40 ml | 24 h 70° C. | in the dark under $N_2$ | 7.0 g |
| Batch 3 | 12.0 g ($2.8 \cdot 10^{-4}$ mol) | 52.0 mg ($5.6 \cdot 10^{-5}$ mol) | ≈30 ml | 24 h 70° C. | in the dark under $N_2$ | 8.4 g |
| Batch 4 | 7.2 g ($1.7 \cdot 10^{-4}$ mol) | 31.2 mg ($3.4 \cdot 10^{-5}$ mol) | ≈20 ml | 24 h 70° C. | in the dark under $N_2$ | 5.1 g |

The amphotericin B-HES conjugates obtained were characterised via their UV spectrum (0.5 g/5 ml $H_2O_{dist.}$) and displayed bands typical of polymeric or micellar interactions of amphotericin B over the range 300–400 nm. Unlike free amphotericin B, which is virtually insoluble in water, the amphotericin-HES conjugates obtained displayed water solubility of >0.1 g/5 ml $H_2O$.

With the aid of LALLS-GPC (Low Angle Laser Light Scattering in combination with Gel Permeation Chromatography), the following GPC characteristics were determined:

| | |
|---|---|
| Weight-determined molecular weight $M_w$: | 102,700 |
| Numerical value for molecular weight: | 36,050 |
| Peak fraction (10%): | 24,050 |
| Base fraction (90%): | 13,800 |

These characteristics essentially matched the characteristics of the HES used.

EXAMPLE 3

Haemolysis Comparison Test of Amphotericin B-HES Conjugate:

The haemolytic action of the ampho-HES preparation according to the invention was determined in comparison with a commercially available amphotericin B-deoxycholate formulation ("Amphotericin B" produced by Bristol-Meyers-Squibb, batch designation: A068), whose active substance is intended to be haemolytic upwards of a concentration of 8 μg/ml (R. Falk et al, Antimicrobial Agents and Chemotherapy, 1999, 1975–1981).

Stock solution for the preparation according to the invention: 11.61 g ampho-HES (corresponding to a weight percentage of 50 mg amphotericin B) were dissolved in 50 ml 5% glucose solution (batch designation: 9233A4 produced by the company Braun Melsungen). The active substance content of the stock solution thus produced was 1 mg amphotericin B per ml. Of this stock solution, three dilutions were produced in accordance with Table 2 and their haemolytic action also investigated.

Commercially available reference preparation (amphotericin B-deoxycholate formulation): a 50 mg bottle was dissolved with 10 ml A.a. injectabilia (batch designation: 0514A63 produced by the company Braun Melsungen) and diluted in 5% glucose solution to 0.12 mg/ml amphotericin B.

Production of the erythrocyte suspension: freshly taken human blood was diluted with approximately 5 times the volume of sterile 0.9% NaCl solution (batch designation: 9055A64 produced by the company Braun Melsungen) and centrifuged for 5 minutes at a relative centrifugal acceleration of 2000. The supernatant solution was then drawn off and the sedimented erythrocytes treated twice more in the same way.

The erythrocytes thus washed were counted in a Neubauer counting chamber and—where necessary—diluted again with sterile 0.9% NaCl solution to a final concentration of approx. $5 \cdot 10^8$ erythrocytes per ml. This suspension is according to DIN standard usable at room temperature for up to 6 hours.

Haemolysis comparison test: 5 ml of the solution to be tested was mixed with 1 ml of the above erythrocyte suspension, transferred to a cleaned centrifuge tube and incubated in a water bath at 37±1° C. for 20 minutes. Centrifuging was then performed for 5 minutes at a relative centrifugal acceleration of 2000.

The extinction of the supernatant liquid was measured. 5 ml of the 0.9% NaCl solution and the 5% glucose solution, which were mixed with 1 ml of the erythrocyte suspension, also incubated at 37±1° C. for 20 minutes and then centrifuged as above, served as negative controls.

For the test for haemolysis, the extinctions of the respective supernatants were measured in a photometer against the negative controls at a wavelength of 576 nm using a cuvette 10 mm in thickness. Owing to the differing stainings of the solutions, the extinction was also measured for the purpose of comparing the solutions without erythrocyte suspension.

The results of the various test batches are summarised in Table 2.

TABLE 2

| Test solution | Concentration of amphotericin B in the solution mg/ml | Concentration of amphotericin B in the test batch mg/ml | Extinction 576 nm | Extinction 576 nm without erythrocytes |
|---|---|---|---|---|
| 0.9% NaCl | — | — | 0.015 | 0.000 |
| 5% glucose | — | — | 0.016 | 0.000 |
| Commercial preparation | 0.12 | 0.1 | 2.271*) | 0.008 |
| Ampho HES | 0.12 | 0.1 | 0.027 | 0.033 |
| Ampho HES | 0.24 | 0.2 | 0.061 | 0.076 |
| Ampho HES | 0.48 | 0.4 | 0.274*) | 0.151 |
| Ampho HES (stock solution) | 1.00 | 0.83 | 2.452*)**) | 0.288 |

*)Solutions in the supernatant red coloured
**)Owing to increased viscosity following centrifuging, erythrocytes still intact microscopically detectable in the supernatant As shown in Table 2, the tested, commercially available amphotericin B-deoxycholate formulation displays a strongly haemolytic action at a concentration of only 0.1 mg/ml in the test batch under the above test conditions. The supernatant had an extinction of 2.271 at 576 nm and was strongly red coloured.

By comparison, no haemolytic action was observable for the ampho-HES preparation according to the invention up to a concentration of 0.2 mg amphotericin B per ml. Only at a concentration of 0.4 mg/ml was slight red staining detectable in the supernatant of the test batch compared with the negative control, which also became noticeable in the extinction values. A slight haemolytic activity accordingly exists at this amphotericin B concentration in the test batch. A strong haemolytic activity as a result of the test preparation was detectable at a concentration of 0.83 mg/ml, where the supernatant was strongly red coloured. In addition, few intact erythrocytes which, owing to the high viscosity during the sedimentation period, were not yet able to sediment into the pellet were still microscopically detectable in the supernatant.

EXAMPLE 4

Synthesis of a Daunorubicin-HES Conjugate:

650 mg ($1.5 \cdot 10^{-5}$ mol) of dried ox-HES (130 kD, degree of oxidation approx. 100%) and 0.8 mg ($3.0 \cdot 10^{-6}$ mol) of daunorubicin were allowed to react in a reaction vessel under the same process conditions as in Example 2 and further treated as in Example 2. Here, too, a reproducible yield of approx. 72% was obtained.

EXAMPLE 5

Synthesis of a Doxorubicin-HES Conjugate:

650 mg ($1.5 \cdot 10^{-5}$ mol) of dried ox-HES (130 kD, degree of oxidation approx. 100%) and 0.8 mg ($3.0 \cdot 10^{-6}$ mol) of doxorubicin were allowed to react in a reaction vessel under the same process conditions as in Example 2 and further treated as in Example 2. The yield achieved was also approx. 70%.

The invention claimed is:

1. Water-soluble antibiotic derivative represented by structural formula (I):

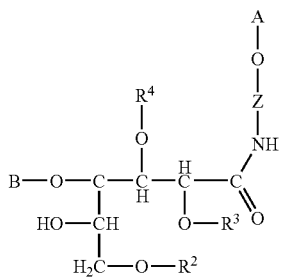

(I)

where:
B=a polymer combined in a 1,4 linkage, selected from the group consisting of hydroxyethyl starch, hydroxypropyl starch, soluble amylose, soluble amylose in hydroxyethylated and/or hydroxypropylated form, soluble amylopectin, and soluble amylopectin in hydroxyethylated and/or hydroxypropylated form,

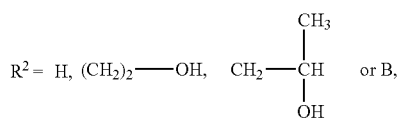

$R^3$, $R^4$ are independently H, —$(CH_2)_2$—OH or

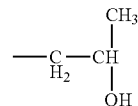

with the conditions that
B=amylose or amylopectin, if $R^2=R^3=R^4=H$
B=hydroxyethyl starch, hydroxyethylated amylopectin or hydroxyethylated amylose, if $R^2$, $R^3$, or $R^4=$ $(CH_2)_2$—OH,
B=hydroxypropyl starch, hydroxypropylated amylopectin or hydroxypropylated amylase, if $R^2$, $R^3$, or

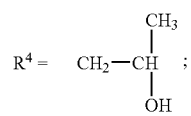

A is

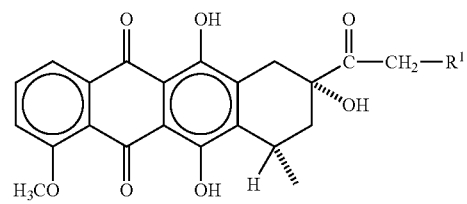

with $R^1=$H or OH or

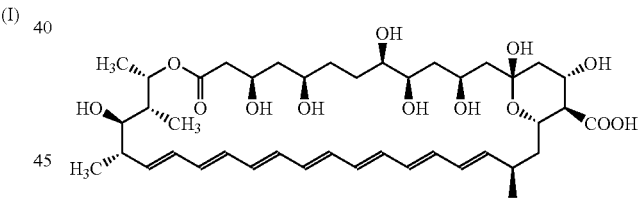

and

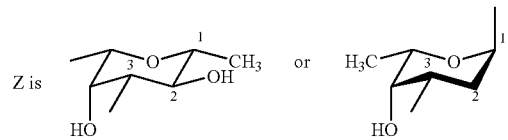

with the condition that if

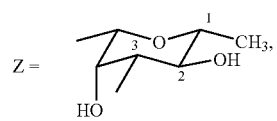

then

A =

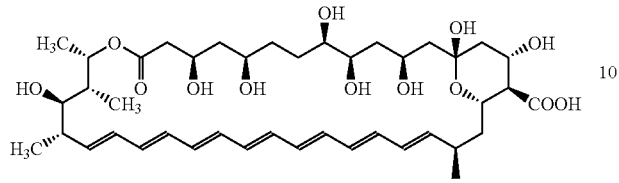

and if

Z = 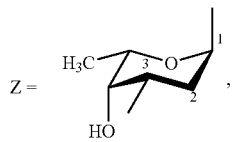, then
A is

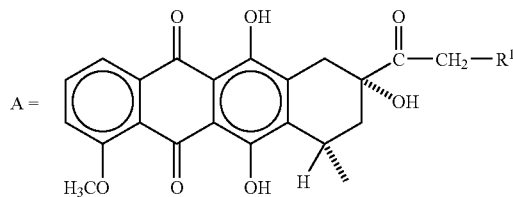

with R¹=H or OH, wherein the group represented by the following structural formula

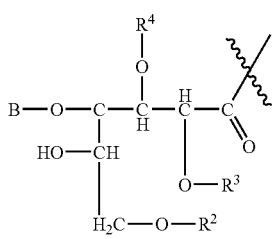

is combined with the amino group at $C_3$ of the amino sugar of the antibiotic with the formation of a peptide bond.

2. Antibiotic derivative according to claim 1 wherein the molar ratio between the antibiotic and the group represented by the following structural formula

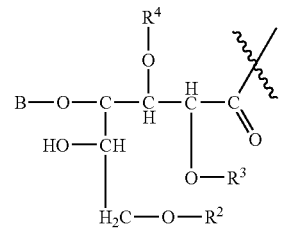

is 1:1.

3. Antibiotic derivative according to claim 1 wherein polymer B is hydroxyethyl starch.

4. Antibiotic derivative according to claim 1 characterised in that the mean molecular weight of the hydroxyethyl starch is in the range between 2000 and $2 \cdot 10^6$ Daltons.

5. Antibiotic derivative according to claim 3 characterised in that the hydroxyethyl starch displays a mean degree of polymerisation of at least 15.

6. Antibiotic derivative according to claim 3 characterised in that the mean molecular weight of the hydroxyethyl starch is >70000 Daltons.

7. Antibiotic derivative according to claim 3 characterised in that the hydroxyethyl starch displays the specification 130/ and a degree of substitution MS in the range 0.1 to 0.8.

8. Antibiotic derivative according to claim 7 characterised in that the hydroxyethyl starch displays a degree of substitutions MS in the range 0.3 to 0.5.

9. Antibiotic derivative according to claim 1 characterised in that the hydroxyethyl starch displays a $C_2/C_6$ substitution ratio in the range 2 to 12.

10. Antibiotic derivative according to claim 9 characterised in that the hydroxyethyl starch displays a $C_2/C_6$ substitution ratio in the range 5 to 11.

11. Antibiotic derivative according to claim 3 characterised in that the hydroxyethyl starch is branched with a α-1,4-glycosidic linkage.

12. Antibiotic derivative according to claim 3 characterised in that the hydroxyethyl starch is branched with a α-1,4-glycosidic linkage and a α-1,6-glycosidic linkage.

13. Antibiotic derivative according to claim 1 characterised in that the antibiotic is amphotericin B.

14. Antibiotic derivative according to claim 1 characterised in that the antibiotic is daunorubicin.

15. Antibiotic derivative according to claim 1 characterised in that the antibiotic is doxorubicin.

16. Method for the preparation of the water-soluble antibiotic derivative according to claim 1 wherein a polysaccharide of structural formula (II)

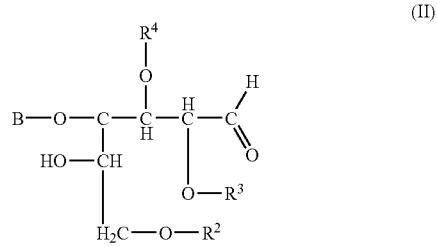

is oxidised at its reducing end in aqueous alkaline solution with the formation of a lactone ring and the product obtained is reacted together with the antibiotic comprising an amino sugar in an organic solvent to form the water-soluble antibiotic derivative.

17. Method according to claim 16 characterised in that the polysaccharide of formula (II) is oxidized at the reducing end with $I_2$.

18. Method according to claim 16 characterised in that dimethyl sulphoxide is used as organic solvent.

19. Method according to claim 16 characterised in that hydroxyethyl starch is used.

20. Method according to claim 19 characterised in that hydroxyethyl starch with a mean molecular weight in the range between 2000 and $2 \cdot 10^6$ Daltons is used.

21. Method according to claim 19 characterised in that a hydroxyethyl starch with a mean degree of polymerisation of at least 15 is used.

22. Method according to claim 19 wherein a hydroxyethyl starch with a mean molecular weight of greater than 70000 Daltons is used.

23. Method according to claim 19 characterised in that a hydroxyethyl starch with the specification 130/ and a degree of substitution MS in the range 0.1 to 0.8 is used.

24. Method according to claim 23 characterised in that a hydroxyethyl starch with a degree of substitution MS in the range 2 to 12 is used.

25. Method according to claim 19 characterised in that a hydroxyethyl starch with a $C_2/C_6$ substitution ratio in the range 2 to 12 is used.

26. Method according to claim 25 characterised in that a hydroxyethyl starch with a $C_2/C_6$ substitution ratio in the range 5 to 11 is used.

27. Method according to claim 19 characterised in that an unbranched hydroxyethyl starch with a α-1,4-glycosidic linkage is used.

28. Method according to claim 19 characterised in that a branched hydroxyethyl starch with a α-1,4-glycosidic linkage and a α-1,6-glycosidic linkage is used.

29. Method according to claim 16 wherein hydroxypropyl starch is used.

30. Method according to claim 16 characterised in that amphotericin B is used as antibiotic.

31. Method according to claim 16 characterised in that daunorubicin is used as antibiotic.

32. Method according to claim 16 characterised in that doxorubicin is used as antibiotic.

33. A method of treating mycotic infections in a subject comprising administering to said subject a therapeutically effective amount of a compound of claim 1, wherein the antibiotic is amphotericin B.

34. The method of claim 33, wherein the polymer B is hydroxyethyl starch.

35. The method of claim 33, wherein the polymer B is hydroxypropyl starch.

36. A method of treating of cancer in a subject, comprising administering to said subject a therapeutically effective amount of a compound of claim 1, wherein the antibiotic is daunorubicine

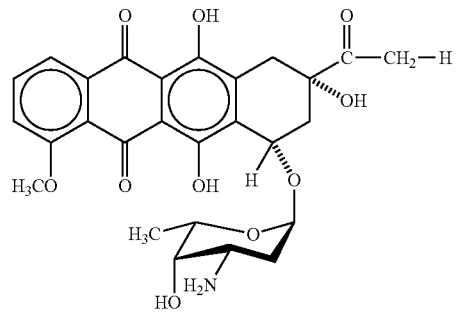

or doxorubicine

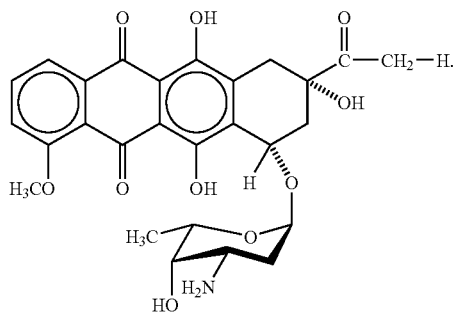

37. The method of claim 36, wherein the antibiotic is daunorubicin.

38. The method of claim 37 wherein the polymer B is hydroxyethyl starch.

39. The method of claim 37 wherein the polymer B is hydroxypropyl starch.

40. The method of claim 36, wherein the antibiotic is doxorubicin

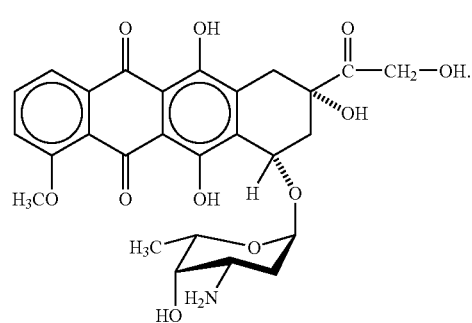

41. The method of claim 40 wherein the polymer B is hydroxyethyl starch.

42. The method of claim 40 wherein the polymer B is hydroxypropyl starch.

* * * * *

UNITED STATES PATENT AND TRADEMARK OFFICE
CERTIFICATE OF CORRECTION

PATENT NO. : 7,115,576 B2
APPLICATION NO. : 10/481597
DATED : October 3, 2006
INVENTOR(S) : Klaus Sommermeyer It is certified that error appears in the above-identified patent and that said Letters Patent is hereby corrected as shown below:

Column 14, line 20, delete " 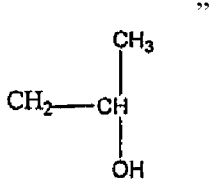 "

and insert -- 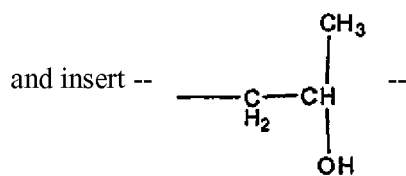 --

Column 15, line 37, delete "

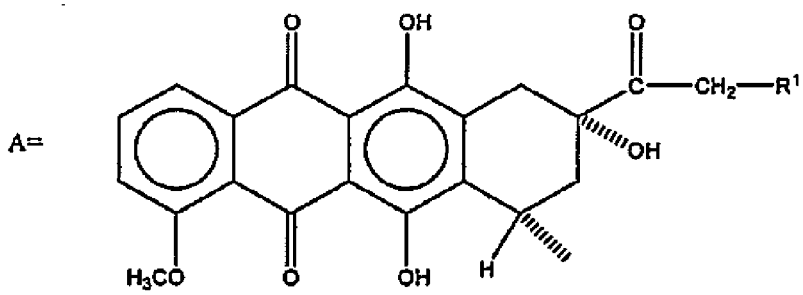

"

UNITED STATES PATENT AND TRADEMARK OFFICE
CERTIFICATE OF CORRECTION

PATENT NO.       : 7,115,576 B2                                            Page 2 of 2
APPLICATION NO.  : 10/481597
DATED            : October 3, 2006
INVENTOR(S)      : Klaus Sommermeyer It is certified that error appears in the above-identified patent and that said Letters Patent is hereby corrected as shown below:

and insert --

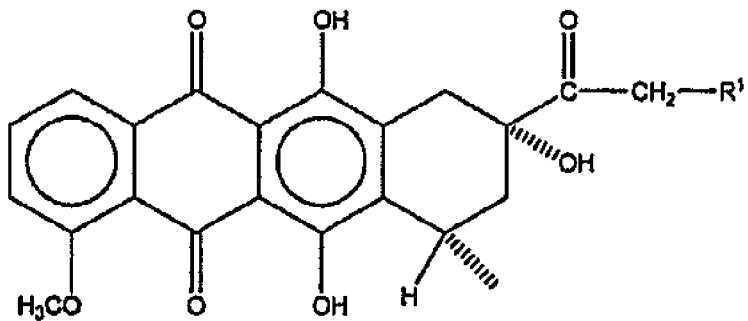

--

Signed and Sealed this

Thirteenth Day of February, 2007

JON W. DUDAS
*Director of the United States Patent and Trademark Office*